United States Patent
Lebel et al.

(10) Patent No.: US 10,635,943 B1
(45) Date of Patent: Apr. 28, 2020

(54) SYSTEMS AND METHODS FOR NOISE REDUCTION IN MEDICAL IMAGES WITH DEEP NEURAL NETWORKS

(71) Applicant: General Electric Company, Schenectady, NY (US)

(72) Inventors: Robert Marc Lebel, Calgary (CA); Dawei Gui, Sussex, WI (US); Graeme Colin McKinnon, Hartland, WI (US)

(73) Assignee: General Electric Company, Schenectady, NY (US)

( * ) Notice: Subject to any disclaimer, the term of this patent is extended or adjusted under 35 U.S.C. 154(b) by 108 days.

(21) Appl. No.: 16/057,738

(22) Filed: Aug. 7, 2018

(51) Int. Cl.
| | |
|---|---|
| G06K 9/62 | (2006.01) |
| G06T 5/00 | (2006.01) |
| G06N 3/08 | (2006.01) |
| G16H 30/40 | (2018.01) |
| G06T 3/00 | (2006.01) |

(52) U.S. Cl.
CPC ......... *G06K 9/6262* (2013.01); *G06K 9/6232* (2013.01); *G06K 9/6257* (2013.01); *G06N 3/08* (2013.01); *G06T 5/002* (2013.01); *G16H 30/40* (2018.01); *G06T 3/0093* (2013.01); *G06T 2207/10081* (2013.01); *G06T 2207/10088* (2013.01); *G06T 2207/10132* (2013.01); *G06T 2207/20081* (2013.01); *G06T 2207/20084* (2013.01)

(58) Field of Classification Search
CPC .. G06K 9/6262; G06K 9/6232; G06K 9/6257; G16H 30/40; G06N 3/08; G06T 5/002
See application file for complete search history.

(56) References Cited

U.S. PATENT DOCUMENTS

| | | | |
|---|---|---|---|
| 10,468,142 B1* | 11/2019 | Abou Shousha | ..... G06T 7/0012 |
| 2014/0201126 A1* | 7/2014 | Zadeh | ................... A61B 5/4803 |
| | | | 706/52 |
| 2016/0224892 A1* | 8/2016 | Sawada | ..................... G06N 3/08 |

(Continued)

OTHER PUBLICATIONS

Welsh, T. et al., "Transferring Color to Greyscale Images," Proceedings of the 29th Annual Conference on Computer Graphics and Interactive Techniques, Jul. 21, 2002, San Antonio, Texas, 4 pages.

(Continued)

*Primary Examiner* — David Bilodeau
(74) *Attorney, Agent, or Firm* — McCoy Russell LLP

(57) ABSTRACT

Methods and systems are provided for reducing noise in medical images with deep neural networks. In one embodiment, a method for training a neural network comprises transforming each of a plurality of initial image data sets not acquired by a medical imaging modality into a target image data set, wherein each target image data set is in a format specific to the medical imaging modality, corrupting each target image data set to generate a corrupted image data set, and training the neural network to map each corrupted image data set to the corresponding target image data set. In this way, the high-resolution of digital non-medical photographs or images can be leveraged for the enhancement or correction of medical images, and the trained neural network can be used to reduce noise and image artifacts in medical images acquired by the medical imaging modality.

20 Claims, 8 Drawing Sheets

(56) References Cited

U.S. PATENT DOCUMENTS

| | | | | |
|---|---|---|---|---|
| 2017/0270653 | A1* | 9/2017 | Garnavi | G06T 7/0002 |
| 2018/0322254 | A1* | 11/2018 | Smurro | H04N 7/152 |
| 2019/0110753 | A1* | 4/2019 | Zhang | G16H 30/40 |
| 2019/0236782 | A1* | 8/2019 | Amit | G16H 30/20 |
| 2019/0251707 | A1* | 8/2019 | Gupta | G06N 3/08 |
| 2019/0362226 | A1* | 11/2019 | Richmond | G06K 9/6256 |

OTHER PUBLICATIONS

Shin, H. et al., "Deep Convolutional Neural Networks for Computer-Aided Detection: CNN Architectures, Dataset Characteristics and Transfer Learning," IEEE Transactions on Medical Imaging, vol. 35, No. 5, May 2016, Published Online Feb. 11, 2016, 14 pages.

Greenspan, H. et al., "Guest Editorial Deep Learning in Medical Imaging: Overview and Future Promise of an Exciting New Technique," IEEE Transactions on Medical Imaging, vol. 35, No. 5, May 2016, Published Online Apr. 29, 2016, 7 pages.

Afridi, M. et al., "Automatic in vivo detection of transplanted cells in MRI using transfer learning paradigm," Proceedings of the 24th Annual Meeting and Exhibition of the International Society for Magnetic Resonance in Medicine (ISMRM), May 7, 2016, Singapore, 3 pages.

Wang, D. et al., "Fast and Robust Detection of Fetal Brain in MRI using Transfer Learning based FCN," Proceedings of the 25th Annual Meeting and Exhibition of the International Society for Magnetic Resonance in Medicine (ISMRM), Apr. 22, 2017, Honolulu, Hawaii, 2 pages.

Knoll, F. et al., "Assessment of the generalization of learned image reconstruction and the potential for transfer learning," Proceedings of the 2018 Joint Annual Meeting of the International Society for Magnetic Resonance & the European Society for Magnetic Resonance in Medicine and Biology (ISMRM-ESMRMB), Jun. 16, 2018, Published Online May 17, 2018, Paris, France, 4 pages.

* cited by examiner

SYSTEMS AND METHODS FOR NOISE REDUCTION IN MEDICAL IMAGES WITH DEEP NEURAL NETWORKS

FIELD

Embodiments of the subject matter disclosed herein relate to medical imaging, such as magnetic resonance imaging (MRI), and more particularly, to reducing noise in medical images.

BACKGROUND

Medical imaging systems are often used to obtain internal physiological information of a subject, such as a patient. For example, a medical imaging system may be used to obtain images of the bone structure, the brain, the heart, the lungs, and various other features of a subject. Medical imaging systems may include magnetic resonance imaging (MRI) systems, computed tomography (CT) systems, x-ray systems, ultrasound systems, and various other imaging modalities.

Typical medical images obtained via any of the above imaging modalities often feature substantial amounts of noise and image artifacts. Reducing or eliminating such noise and image artifacts for a given imaging modality typically requires careful consideration of the physics of the imaging modality, and a set of algorithms may be developed and implemented for addressing and correcting specific types of image noise and specific types of image artifacts.

BRIEF DESCRIPTION

In one embodiment, a method for training a neural network comprises transforming each of a plurality of initial image data sets not acquired by a medical imaging modality into a target image data set, wherein each target image data set is in a format specific to the medical imaging modality, corrupting each target image data set to generate a corrupted image data set, and training the neural network to map each corrupted image data set to the corresponding target image data set. In this way, the high-resolution of digital non-medical photographs or images can be leveraged for the enhancement or correction of medical images, and the trained neural network can be used to reduce noise and image artifacts in medical images acquired by the medical imaging modality.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 6:
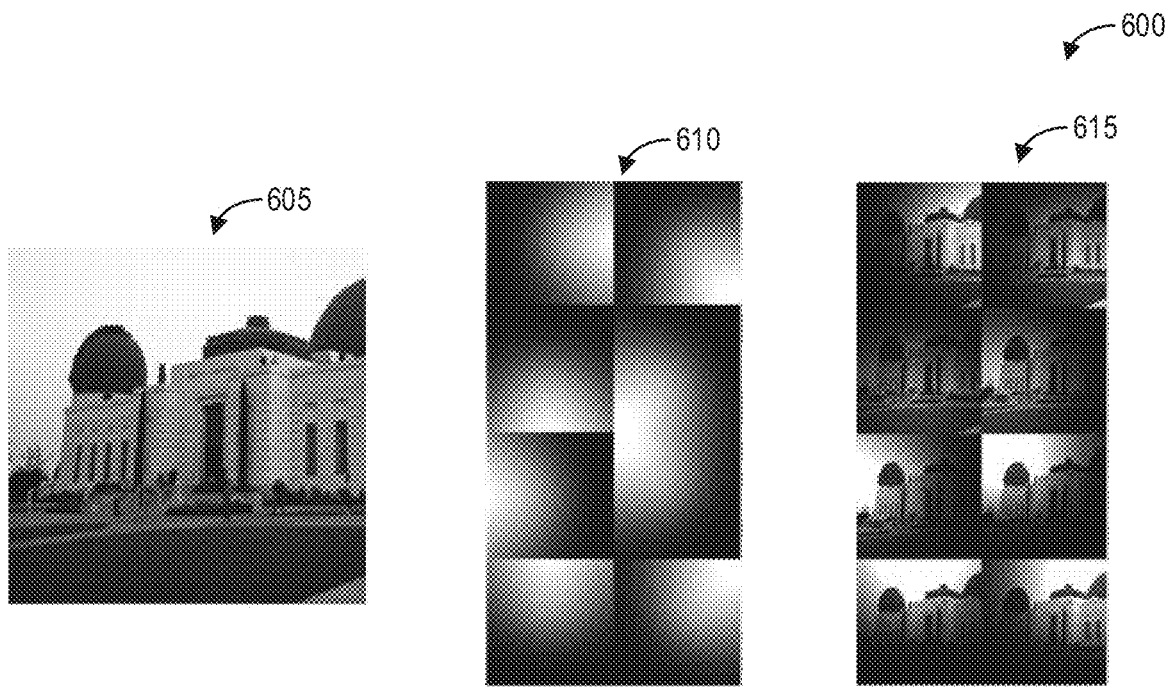
FIG. 6 pictorially depicts an example transformation of a digital photograph into an MR-like image according to an embodiment.
Figure 7:
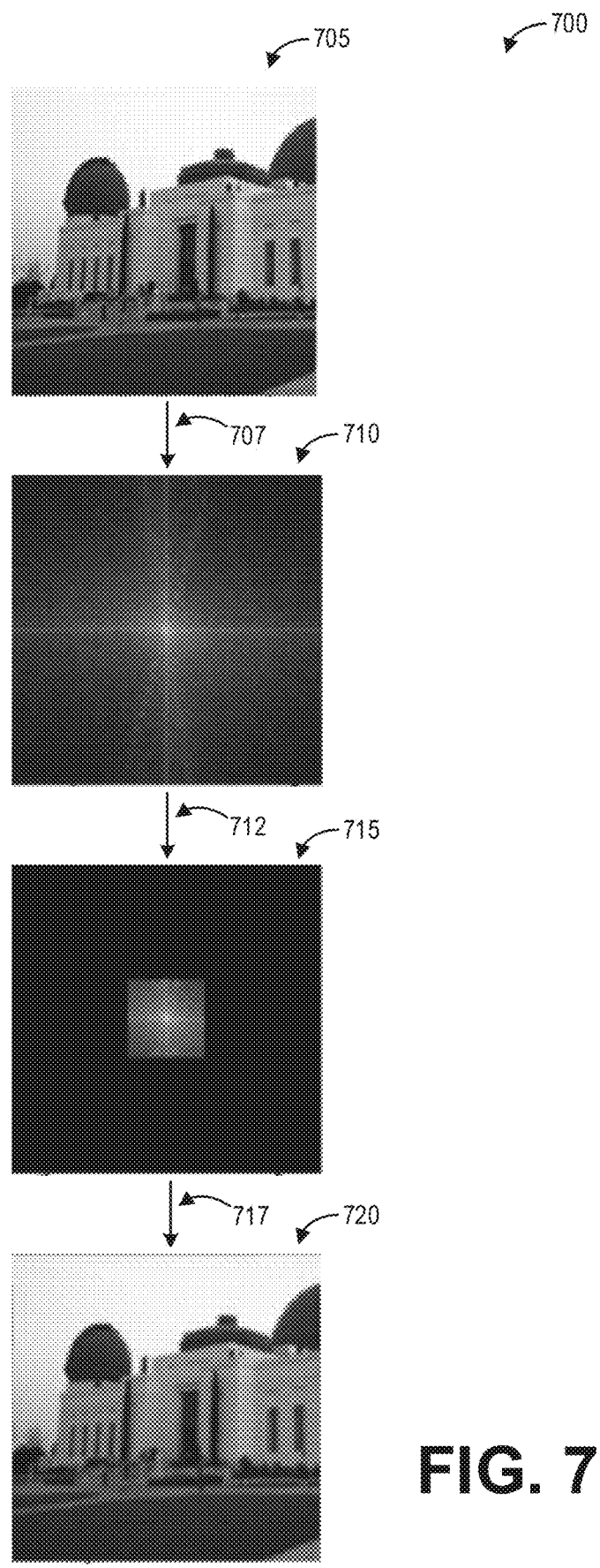
FIG. 7 pictorially depicts an example method for transforming an MR-like image into a corrupted image according to an embodiment.
Figure 8:
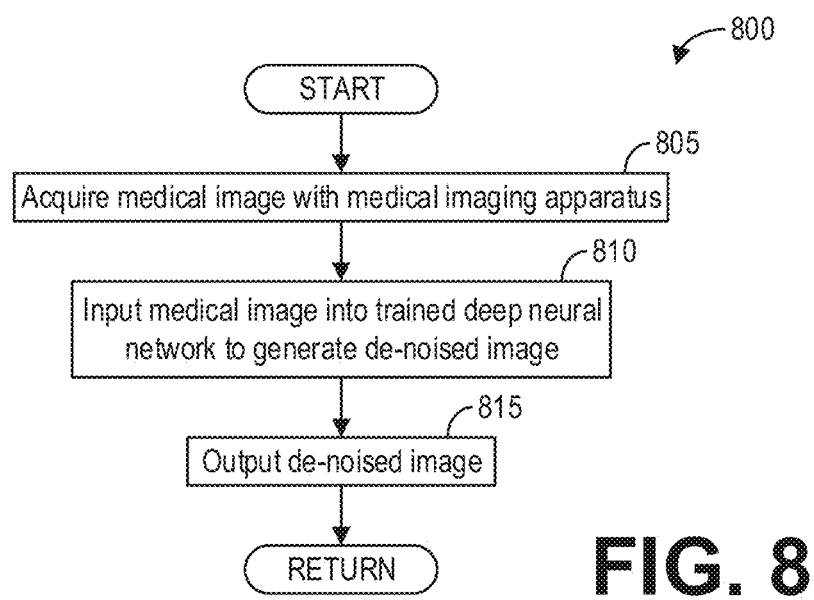
FIG. 8 shows a high-level flow chart illustrating an example method for processing an image data set acquired by a medical imaging system with a trained neural network according to an embodiment.
Figure 9:
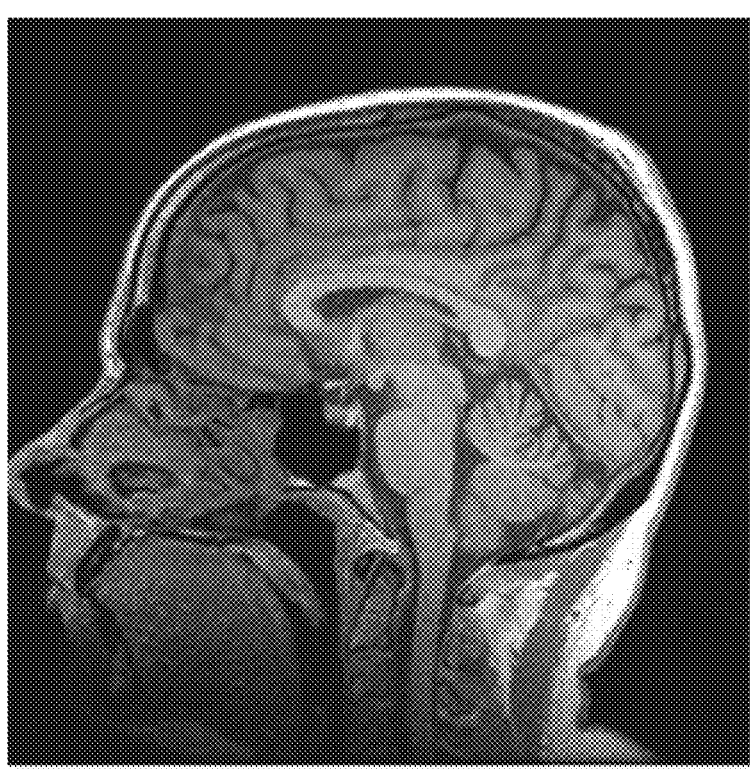
FIG. 9 shows a typical image acquired by an MR imaging system according to an embodiment.
Figure 10:
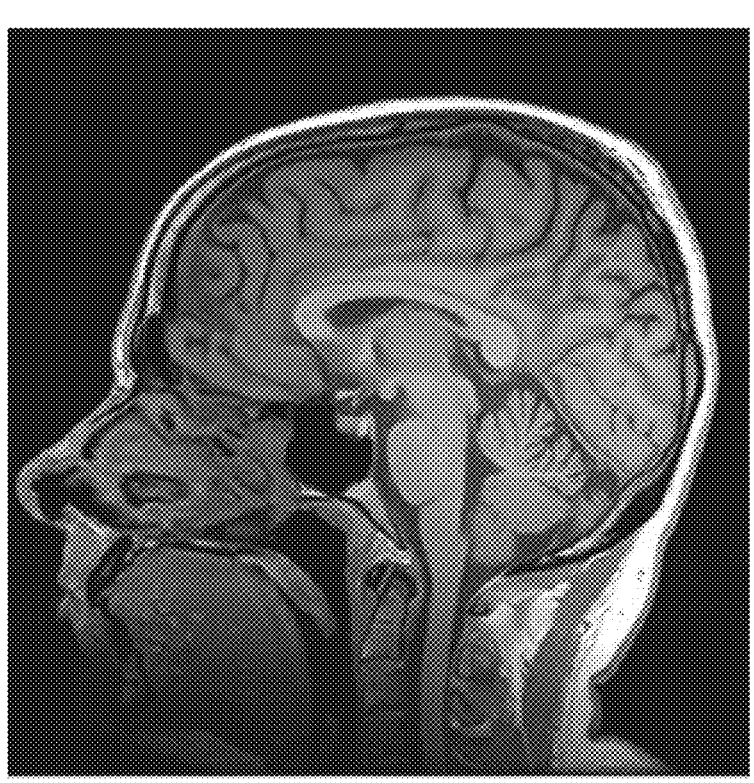
FIG. 10 shows the example image of FIG. 9 after being processed with a trained neural network according to an embodiment.

The following description relates to various embodiments of image noise reduction for medical imaging systems. In particular, systems and methods are provided for reducing or eliminating image noise and image artifacts with a deep neural network system for images of a subject acquired with a medical imaging system, such as the MRI system depicted in FIG. 1. A deep neural network, such as the deep neural network depicted in FIG. 2, includes a large plurality of neurons or nodes, such as the neuron depicted in FIG. 3, arranged into layers. The deep neural network is trained with a plurality of image data sets not acquired by a medical imaging modality. For example, the plurality of image data sets may be acquired by digital cameras and can be presented as digital photos or video frames. As used herein, a "medical imaging modality" refers to a type of medical imaging technology, such as MR, CT, X-ray, ultrasound, PET, etc. A medical imaging modality is a general term for a type of medical imaging systems of various models made by various manufacturers. The trained neural network is then used to enhance or correct images acquired by medical imaging systems. In particular, a photograph or video frame not acquired by an imaging modality is transformed into a medical-like image and the medical-like image is then transformed into a corrupted image, as depicted in FIG. 4. A method for training the deep neural network, such as the method depicted in FIG. 5, includes transforming a plurality of image data sets not acquired by a medical imaging modality to generate a plurality of target image data sets in a format specific to the medical imaging modality, and corrupting the plurality of target image data sets to generate a plurality of corrupted image data sets. The deep neural network is then trained to map the plurality of corrupted image data sets to the plurality of target image data sets. An example transform that converts an image data set not acquired by a medical imaging modality into a target image data set in a format specific to the imaging modality is depicted in FIG. 6. An example transform that converts a target image data set into a corrupted image data set with particular types of noise according to the imaging modality is depicted in FIG. 7. A method for de-noising a medical image, such as the method depicted in FIG. 8, thus includes inputting an acquired medical image data set into the trained deep neural network. As depicted in FIGS. 9 and 10, such a deep neural network effectively reduces noise and image artifacts.

While the methods for noise reduction with deep neural networks are described herein with regard to an MRI system in most of the disclosure, it should be appreciated that the methods may be implemented with other imaging modalities. For example, while the system of FIG. 1 specifically illustrates an MRI apparatus, the methods described herein may be implemented with ultrasound imaging devices, CT imaging systems, and other imaging modalities. Specific examples of how to adapt the methods herein for different medical imaging apparatuses or systems are described further herein.

Figure 1:
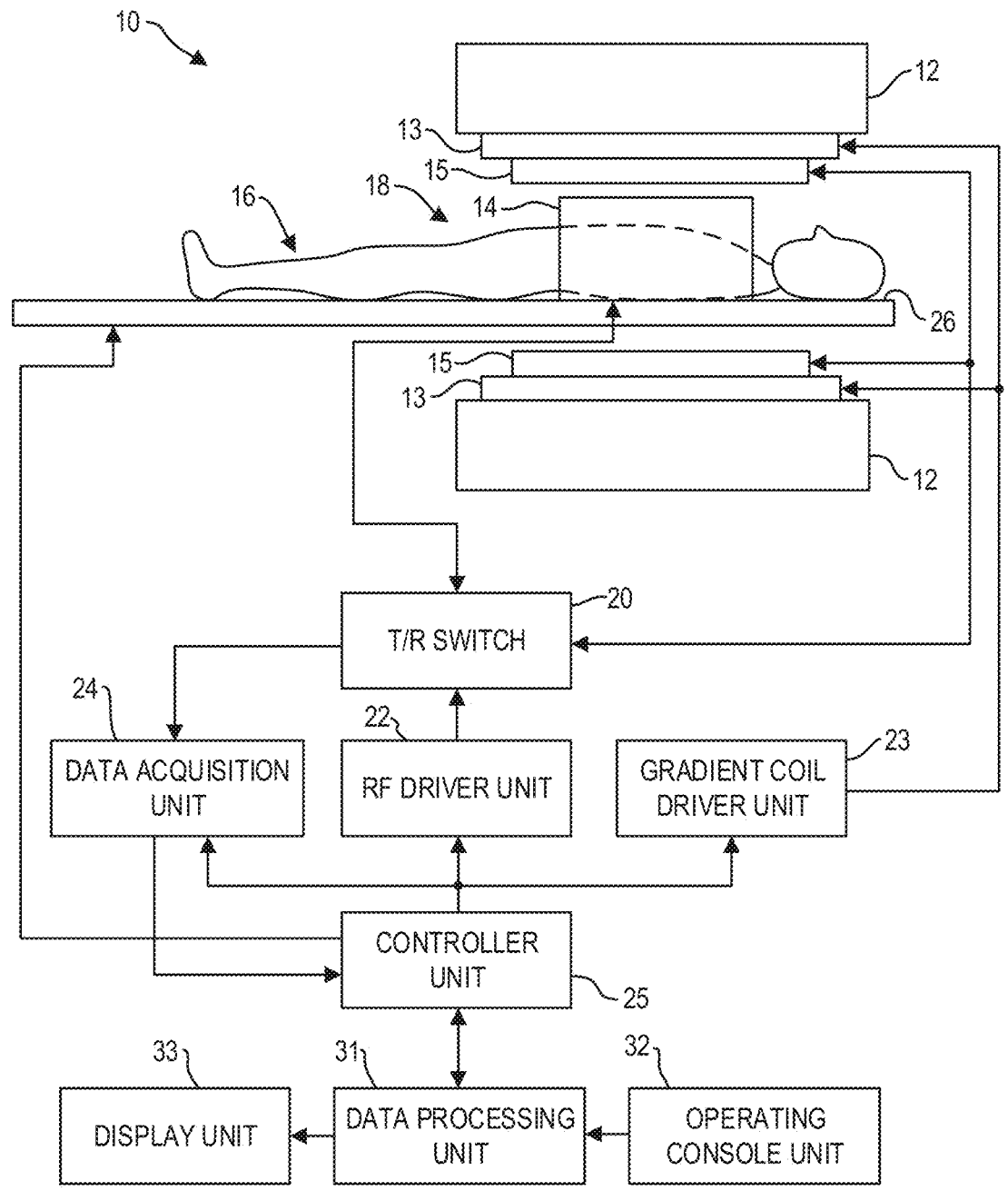
FIG. 1 is a block diagram of an MRI system according to an exemplary embodiment.

FIG. 1 illustrates a magnetic resonance imaging (MRI) apparatus 10 that includes a magnetostatic field magnet unit 12, a gradient coil unit 13, an RF coil unit 14, an RF body coil unit 15, a transmit/receive (T/R) switch 20, an RF driver unit 22, a gradient coil driver unit 23, a data acquisition unit 24, a controller unit 25, a patient bed 26, a data processing unit 31, an operating console unit 32, and a display unit 33. The MRI apparatus 10 transmits electromagnetic pulse signals to a subject 16 placed in an imaging space 18 with a magnetostatic field formed to perform a scan for obtaining magnetic resonance (MR) signals from the subject 16 to reconstruct an image of a slice of the subject 16 based on the MR signals thus obtained by the scan.

The magnetostatic field magnet unit 12 includes, for example, typically an annular superconducting magnet, which is mounted within a toroidal vacuum vessel. The magnet defines a cylindrical space surrounding the subject 16, and generates a constant primary magnetostatic field $B_0$.

The MRI apparatus 10 also includes the gradient coil unit 13 that generates a gradient magnetic field in the imaging space 18 so as to provide the MR signals received by the RF coil unit 14 with three-dimensional positional information. The gradient coil unit 13 includes three gradient coil systems, each of which generates a gradient magnetic field which includes into one of three spatial axes perpendicular to each other, and generates a gradient field in each frequency-encoding direction, phase-encoding direction, and slice-selection direction in accordance with the imaging condition. More specifically, the gradient coil unit 13 applies a gradient field in the slice-selection direction (or scan direction) of the subject 16, to select the slice; and the RF coil unit 14 transmits an RF pulse to a selected slice of the subject 16 and excites it. The gradient coil unit 13 also applies a gradient field in the phase-encoding direction of the subject 16 to phase encode the MR signals from the slice excited by the RF pulse. The gradient coil unit 13 then applies a gradient field in the frequency-encoding direction of the subject 16 to frequency encode the MR signals from the slice excited by the RF pulse.

The RF coil unit 14 is disposed, for example, to enclose the region to be imaged of the subject 16. In the static magnetic field space or imaging space 18 where a static magnetic field $B_0$ is formed by the magnetostatic field magnet unit 12, the RF coil unit 14 transmits, based on a control signal from the controller unit 25, an RF pulse that is an electromagnetic wave to the subject 16 and thereby generates a high-frequency magnetic field $B_1$. This excites a spin of protons in the slice to be imaged of the subject 16. The RF coil unit 14 receives, as an MR signal, the electromagnetic wave generated when the proton spin thus excited in the slice to be imaged of the subject 16 returns into alignment with the initial magnetization vector. In one embodiment, the RF coil unit 14 may transmit and receive an RF pulse using the same RF coil. In another embodiment, the RF coil unit 14 may be used for only receiving the MR signals, but not transmitting the RF pulse.

The RF body coil unit 15 is disposed, for example, to enclose the imaging space 18, and produces RF magnetic field pulses $B_1$ orthogonal to the main magnetic field $B_0$ produced by the magnetostatic field magnet unit 12 within the imaging space 18 to excite the nuclei. In contrast to the RF coil unit 14, which may be easily disconnected from the MR apparatus 10 and replaced with another RF coil unit, the RF body coil unit 15 is fixedly attached and connected to the MRI apparatus 10. Furthermore, whereas local coils such as those comprising the RF coil unit 14 can transmit to or receive signals from only a localized region of the subject 16, the RF body coil unit 15 generally has a larger coverage area and can be used to transmit or receive signals to the whole body of the subject 16. Using receive-only local coils and transmit body coils provides a uniform RF excitation and good image uniformity at the expense of high RF power deposited in the subject 16. For a transmit-receive local coil, the local coil provides the RF excitation to the region of interest and receives the MR signal, thereby decreasing the RF power deposited in the subject 16. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in a receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coil unit 14 or the RF body coil unit 15 and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 14 or the RF body coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a preamplifier (not shown), a phase detector (not shown), and an analog/digital converter (not shown) used to acquire the MR signals received by the RF coil unit 14. In the data acquisition unit 24, the phase detector phase detects, using the output from the RF oscillator of the RF driver unit 22 as a reference signal, the MR signals received from the RF coil unit 14 and amplified by the preamplifier, and outputs the phase-detected analog MR signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as, as non-limiting examples, a keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform pre-determined data processing is recorded. The data processing unit 31 is connected to the controller unit 25 and performs data processing based on control signals received from the controller unit 25. The data processing unit 31 is also connected to the data acquisition unit 24 and generates spectrum data by applying various imaging processing operations to the MR signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a slice image of the subject 16 generated by the data processing unit 31.

The MRI apparatus 10 may be configured with a deep learning system for reducing image noise and image artifacts in images acquired via the MRI apparatus 10. In some embodiments, the deep learning system may be implemented on an edge device (not shown) connected to the MRI apparatus 10. In some embodiments, the deep learning system may be implemented remotely, for example in a cloud in communication with the MRI apparatus 10. In some embodiments, portions of the deep learning system are implemented on different devices, such as any appropriate combination of the MRI apparatus 10, the edge device, the cloud, etc.

Figure 2:
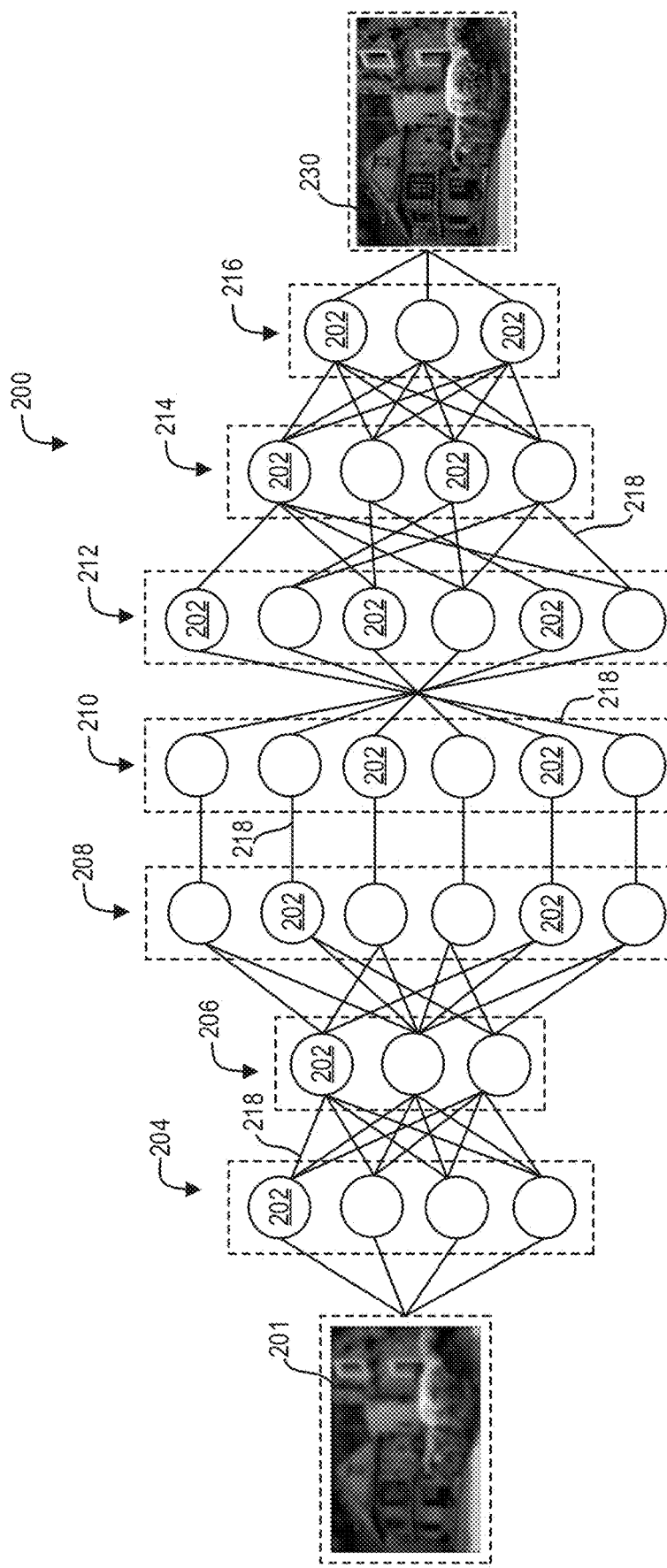
FIG. 2 shows a schematic diagram illustrating an example neural network according to an embodiment.

As an illustrative example, FIG. 2 depicts a neural network 200 having one or more nodes/neurons 202 which, in some embodiments, may be disposed into one or more layers 204, 206, 208, 210, 212, 214, and 216. The neural network 200 may be a deep neural network. As used herein with respect to neurons, the term "layer" refers to a collection of simulated neurons that have inputs and/or outputs connected in similar fashion to other collections of simulated neurons. Accordingly, as shown in FIG. 2, the neurons 202 may be connected to each other via one or more connections 218 such that data may propagate from an input layer 204, through one or more intermediate layers 206, 208, 210, 212, 214 to an output layer 216.

Figure 3:
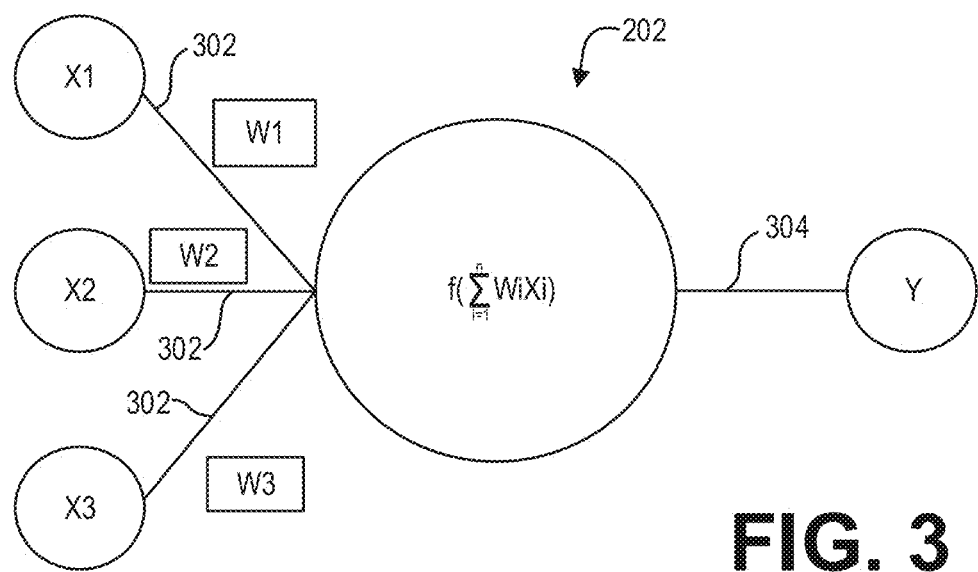
FIG. 3 shows a schematic diagram illustrating an example node of a neural network according to an embodiment.
Figure 4:
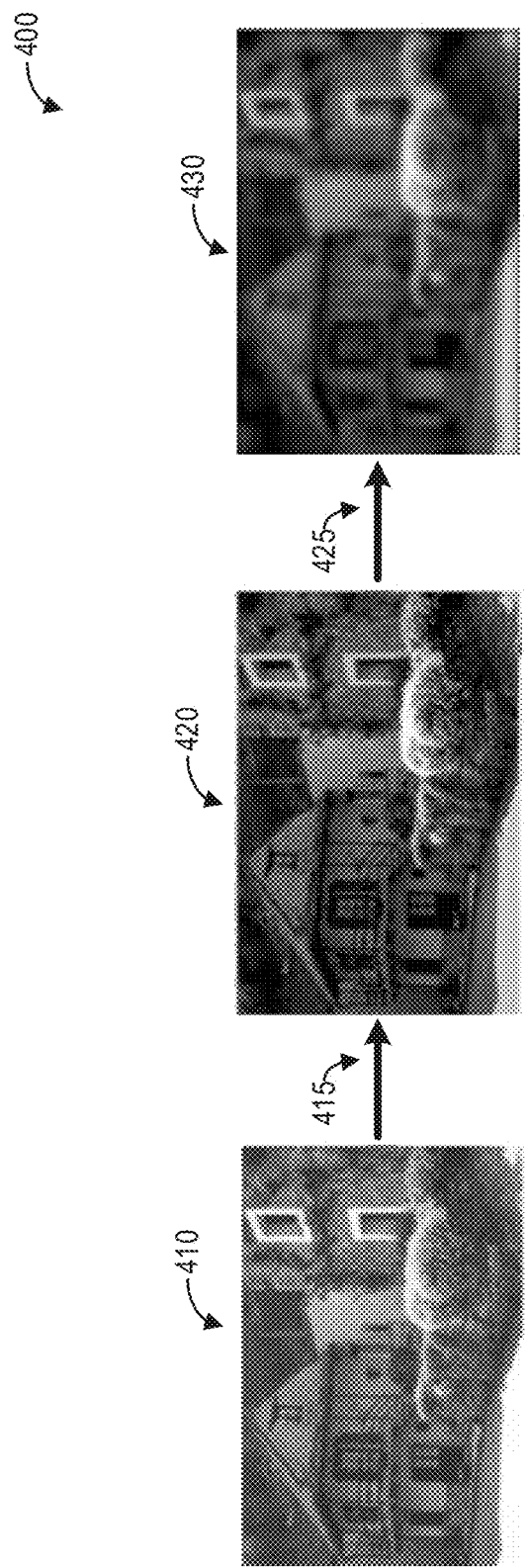
FIG. 4 pictorially depicts an example method for preparing a training dataset for a deep neural network according to an embodiment.

FIG. 3 shows input and output connections for a neuron in accordance with an exemplary embodiment. As shown in FIG. 3, the connections 218 of an individual neuron 202 may include one or more input connections 302 and one or more output connections 304. Each input connection 302 of a neuron 202 may be an output connection of a preceding neuron, and the output connections 304 of the neuron 202 may be an input connection of one or more subsequent neurons. While FIG. 3 depicts a neuron 202 as having a single output connection 302, it should be understood that neurons may have multiple output connections that transmit/pass the same value. In embodiment, the neurons 202 may be data constructs, e.g., structures, instantiated class objects, matrices, etc., and the input connections 218 may be received by the neuron 202 as weighted numerical values, e.g., floating point or integer values. For example, as further shown in FIG. 3, input connections X1, X2, and X3 may be weighted via weights W1, W2, and W3, respectively, summed, and sent/transmitted/passed as output connection Y. As will be appreciated, the processing of an individual neuron 202 may be represented, generally, by the equation:

$$Y = f\left(\sum_{i=1}^{n} WiXi\right)$$

where n is the total number of input connections 302 to the neuron 202. In embodiment, the value of Y may be based at least in part on whether the summation of WiXi exceeds a threshold. For example, Y may have a value of zero (0) if the summation of the weighted inputs fails to exceed a desired threshold.

As will be further understood, the input connections 302 of neurons 202 in the input layer 204 may be mapped to the input 201, while the output connections 302 of the neurons 202 in the output layer 216 may be mapped to the output 230. As used herein, "mapping" an input connection 302 to the input 201 refers to the manner by which the input 201 affects/dictates the value of the input connections 302. Similarly, as also used herein, "mapping" an output connection 302 to the output 230 refers to the manner by which the value of the output connections 302 affects the output 230.

Accordingly, in embodiments, the acquired/obtained input 201 is passed/fed to the input layer 204 of the neural network 200 and propagated through the layers 204, 206, 208, 210, 212, 214, and 216 such that mapped output connections 304 of the output layer 216 generates/corresponds to the output 230.

The deep neural network 200 may be trained using pairs of noise-free image data sets and corrupted image data sets acquired via a medical imaging apparatus such as the MRI apparatus 10, such that medical images with noise may be input to the deep neural network 200, which in turn outputs a noise-reduced medical image. However, it is challenging to obtain ideal target medical images that are free of noise and artifacts. Images not acquired by an imaging modality, e.g., digital photographs, can be high resolution, low noise, and abundant. As discussed further herein, digital photographs of various contents (e.g., non-medical contents such as houses, vehicles, landscapes, animals, plants, and medical contents such as pathology slides and anatomical structures) may be used to train the deep neural network 200 to reduce noise in medical images. To that end, such initial image data sets are first transformed to a format specific to the medical imaging modality and then corrupted to provide input and target output image data sets for training the deep neural network 200.

As an illustrative example, FIG. 4 pictorially depicts an example method 400 for preparing a training dataset for a deep neural network such as the neural network 200 for processing medical images according to an embodiment. The method 400 includes applying a first transform 415 to an image data set not acquired by a medical imaging modality, which may be presented as, for example, a digital photograph 410 to create or generate a target image data set in a format specific to an imaging modality, which may be presented as an ideal MR-like target image 420. The method 400 then applies a second transform 425 to corrupt the target image data set to generate a corrupted image data set, which may be presented as a corrupted image 430.

As described further herein, the first transform 415 and the second transform 425 are modality-specific, and each transform may comprise composite operations consisting of one or more sub-transforms. The first transform 415 and the second transform 425 are not necessarily linear or invertible. As an example, the first transform 415 may include re-mapping color channels or grayscale channels of the initial image 410 to either a physical parameter representing the object being imaged (i.e., density) or to the response of the imaging system. Such a parametric mapping may be used in some examples in a physical model to further compute or simulate the signal response of the imaging system. Thus, in this way, the first transform 415 converts the digital photograph 410 into a target image 420 that resembles an ideal medical image.

The second transform 425 converts the perfect or target medical-like image into one that is typically obtained according to the imaging modality. The second transform 425 thus typically introduces noise, artifacts, and/or other typical responses of the imaging system.

Thus, a method for training a deep neural network to reduce noise in medical images includes applying a first transform to a digital photograph to generate a medical-like image, and applying a second transform to the medical-like image to generate a corrupted image. It should be appreciated that "digital photographs" are used as an example in most part of the disclosure, other types of images not acquired by an imaging modality can also be used, for example, video frames.

Although one photograph 410 is depicted in FIG. 4, it should be appreciated that a large plurality of photographs may be prepared as described herein for training a deep neural network.

Figure 5:
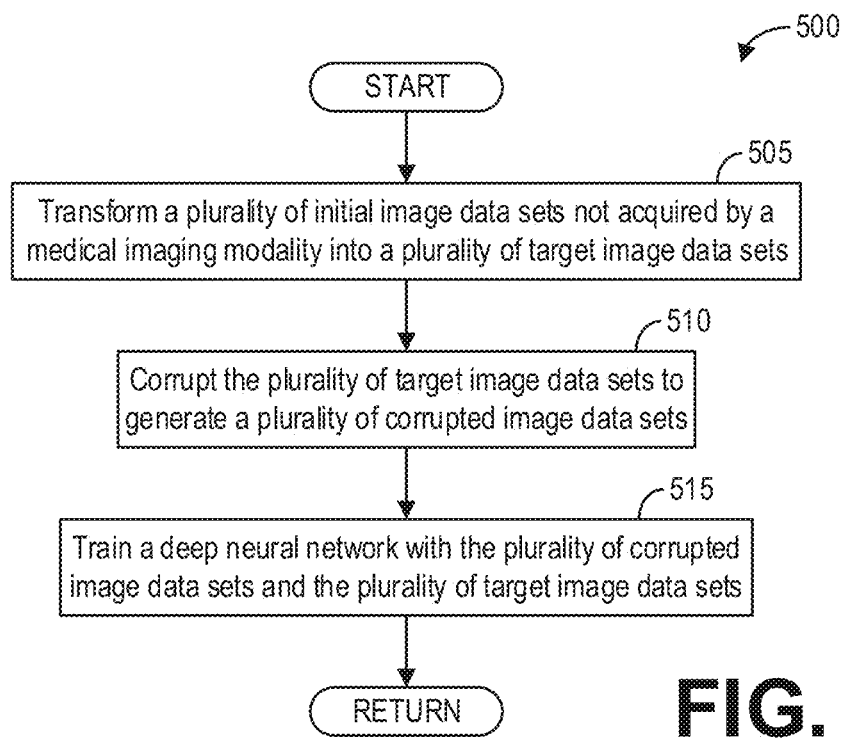
FIG. 5 shows a high-level flow chart illustrating an example method for training a deep neural network according to an embodiment.

FIG. 5 shows a high-level flow chart illustrating an example method 500 for training a deep neural network according to an embodiment. Method 500 is described with regard to the systems and components of FIGS. 1-3, though it should be appreciated that the method 500 may be implemented with other systems and components without departing from the scope of the present disclosure. In some embodiments, method 500 may be implemented as executable instructions in any appropriate combination of the MRI apparatus 10, an edge device connected to the MRI apparatus 10, a cloud in communication with the MRI apparatus 10, and so on.

Method 500 begins at 505. At 505, a plurality of initial image data sets not acquired by a medical imaging modality are transformed into target image data sets that are in a format specific to the medical imaging modality. The transform comprises one or more operations, as discussed below.

In some embodiments, the initial image data sets were acquired by digital cameras and can be presented as digital photographs. The initial image data sets may be in a digital photographic format, such as red-green-blue (RGB), cyan-magenta-yellow-black (CMYB), hue saturation brightness (HSB), grayscale, etc. For training a deep neural network to process magnetic resonance (MR) images, the initial images data sets are transformed to a format specific to MR, such as images of complex values, images of real values, MR parametric maps, and so on. In further embodiments, more operations of transform can be performed. For example, the parametric map may be converted to images of numerical values, linear or non-linear background phase may be added, Fourier truncation may be performed, spatial warping may be added, and/or the replication and addition of coil sensitivities may be applied. The parametric maps that may be used for signal modeling in the context of MRI may include but are not limited to one or more of proton density, relaxation time (e.g., T1, T2, T2*, T1rho), magnetic susceptibility, chemical shift, temperature, and diffusivity.

As another example, for training the deep neural network to process ultrasound images, the initial images data sets are transformed to a format specific to ultrasound, such as ultrasound parametric maps, image data sets of positive real value, etc. In further embodiments, more operations of transform can be performed. For example, the parametric maps may be converted to image data sets of numerical values, and/or spatial warping may be added. The parametric maps that may be used for signal modeling in the context of ultrasound include but are not limited to one or more of acoustic impedance, velocity, and density.

As yet another example, for training the deep neural network to process computed tomography (CT) images, the initial images data sets are transformed to a format specific to CT, such as image data sets of positive real values, CT parametric map, etc. In further embodiments, more operations of transform can be performed. For example, the parametric maps may be converted to image data sets of numerical values. The parametric maps that may be used for signal modeling in the context of CT include but are not limited to radiation absorption (e.g., in Hounsfield units).

For example, to convert a color or grayscale photograph to a complex-valued MR image, method 500 may map each color channel (e.g., red, green, and blue) or grayscale channel to the complex plane, and then combines each channel into a single image. For example, the complex-valued image data set $I_m$ may be obtained according to the equation:

$$I_m = \sum_j a_j I_j e^{i\phi_j},$$

where $I_m$ is the desired complex-valued image data set, j is the index over color or grayscale channels, $a_j$ is a scale factor for the jth channel, $I_j$ is the values of the jth channel, and $\phi_j$ is the phase angle for the jth channel. This formulation takes each color or grayscale channel, scales it, assigns it a phase on the complex plane, and then sums all channels together. It should be appreciated that more elaborate approaches for making each channel complex may be used herein. For example, the phase term $\phi_j$ could be changed from a per-channel constant value to a variable that changes within each image.

As mentioned above, in further examples, the transform may include adding linear or non-linear background phase. For example, MR images frequently feature a linear background phase ramp. A similar phase may be introduced according to the following equation:

$$I_m(x,y)=I(x,y)e^{i(\phi_x x+\phi_y y+\phi_0)},$$

where $I_m(x, y)$ is the complex value at pixel location (x, y), I(x, y) is the value at pixel location (x, y) of the input image (i.e., the digital photograph), $\phi_x$ and $\phi_y$ are the rate of phase change per pixel in the x and y directions, respectively, and $\phi_0$ is a baseline phase shift. The parameters $\phi_x$, $\phi_y$, and $\phi_0$ may be predetermined or randomly defined. Non-linear phase could be introduced to the photographs in a similar manner, for example, by using a general polynomial in the exponential term. In some embodiments, a linear phase ramp may be obtained by applying a spatial shift in the Fourier domain, per the Fourier shift theorem.

As another example, the digital photographic data sets are transformed into a parametric map. Parametric maps are either imaging endpoints or are used to simulate endpoints. There are numerous modality-specific parametric maps. Such parametric maps are typically real-valued parameters related to a physical quantity (such as flow velocity, proton density, and so on) that can be measured (directly or indirectly) with an imaging device. Thus, one approach includes first selecting a color channel or combining multiple channels to obtain a grayscale image, and then re-mapping the intensity range to the relevant range for the parameter of interest. From a single-channel image (either one color channel or a grayscale composite), a parametric map P at pixel (x, y) may be obtained via the equation:

$$P(x,y)=S(I(x,y)-C),$$

where S is a scale factor and C is a shift. The scale and shift parameters are based on the range of the parametric map to the model.

When parametric maps, for example obtained via the above procedure, are not the end-point, they may be used to simulate the imaging system's response to the parameters. That is, the color or grayscale photographs are converted to intermediate parametric maps, which can then be used to simulate or compute the synthetic medical-like image according to the imaging device or modality. The specific simulation depends on the modality, acquisition mode, and parametric maps of interest. As one example, a map of the acoustic density (derived from a medical image) may be used to predict acoustic reverberation patterns observed in ultrasound images. As another example, a map of Hounsfield units or linear attenuation coefficients may be used to synthesize an image with streak artifacts due to beam hardening and scatter. As yet an example, beginning with an image representing the magnetic susceptibility $\chi$, derived from a medical image, as well as knowledge of the MRI echo time (TE), the observed image phase as measured with MRI may be simulated by the following equation:

$$\Phi(TE) = \frac{\gamma}{2\pi} TE \cdot (d * \chi),$$

where d is the dipole kernel and $\gamma$ is the gyromagnetic ratio.

As another illustrative and non-limiting example, FIG. 6 pictorially depicts an example transformation 600 of a digital photograph 605 into an MR-like image 615 by the replication and addition of coil sensitivities. Magnetic resonance images are frequently acquired with multiple receiver coils that are sensitive to different parts of the object. Coil sensitivities, such as the illustrated coil sensitivities 610, may be obtained from actual measurements with the MRI apparatus 10, simulated via electromagnetic models, or fabricated from analytic approximations. As depicted in the transformation 600, the single input image (i.e., the digital photograph 605) is replicated, and a spatial weighting is applied to each replicated image to convert the non-medical photograph 605 into a multi-coil MR-like image set or medical-like image 615. Mathematically, the transformation 600 may be expressed as $$I_m = SI,$$

where I is an n×1 vector of all pixel values in the original image (consisting of a total of n pixels), S is the coil sensitivity matrix of size $n_c$×n (representing $n_c$ coils), and $I_m$ is an $n_c$×n representation of the multi-coil images.

As mentioned above, the first transform applied at 505 may include one or more of the operations described hereinabove, such that each of the plurality of image data sets not acquired by a medical imaging modality are transformed into a plurality of target image data set in a format specific to the medical imaging modality.

Referring again to FIG. 5, after the plurality of initial image data sets are transformed into corresponding target image data sets, method 500 continues to 510. At 510, each target image data set is corrupted to generate a corresponding corrupted image data set. The corruption comprises one or more operations that map the target image data set (which can be presented as an ideal medical-like image) into a corresponding corrupted image (which can be presented as a medical image with noise/artifacts). The corrupted image simulates a typical medical image acquired with an imaging system, and thus includes noise and/or image artifacts that may be introduced during imaging.

For example, for training a deep neural network to process MR images, the corruption may include but is not limited to one or more of applying Fourier truncation, spatial warping, random noise, spatial shifts, intensity changes (based on previously-assigned properties), phase changes (based on previously-assigned properties), additional pathology, additional blurring, conversion to and from the Fourier domain, additional ringing, converting a parametric map to a numerical value, and the replication and addition of coil sensitivities. It should be appreciated that in some examples, similar operations may be performed when transforming the initial image data sets into target image data sets as well as when corrupting the target image data sets. For example, transforming an initial image data set into a target image data set may include the replication and addition of coil sensitivities, such that the target image data set comprises a multi-coil MR-like image data set as described hereinabove with regard to FIG. 6, while additional coil sensitivities may be added when corrupting the target image data set. As another example, spatial warping and/or Fourier truncation may be applied during both the transformation and the corruption steps, as even the most ideal MR image may exhibit some spatial warping or Fourier truncation, though varying levels of warping and/or truncation may be applied during the different steps (e.g., more substantial or extreme Fourier truncation and spatial warping may be applied during the corruption step relative to the amount of Fourier truncation and spatial warping applied during the initial transformation).

As another example, for training a deep neural network to process ultrasound images, the corruption may include but is not limited to one or more of applying spatial shading, random noise, speckle, additional pathology, additional blurring, spatial warping, and converting a parametric map to numerical values.

For training a deep neural network to process CT images, the corruption may include but is not limited to one or more of applying streak artifacts, random noise, ring artifacts, additional pathology, additional blurring, and converting a parametric map to numerical values.

For example, medical images are universally corrupted by random noise. The specific type of noise depends on the imaging modality and reconstruction method. Mathematically, this corresponds to $$I_m = I + \epsilon,$$

where $I_m$ is the output image with additive noise (i.e., the corrupted image data set), I is the clean input image (i.e., the target image data set), and E is the additive noise. In MRI, for example, images may be corrupt with complex-valued, white, Gaussian noise. In magnitude or ultrasound images, the noise may comprise Rician noise. In CT imaging, the noise may comprise Poisson noise. To that end, the additive noise E may be modeled according to Gaussian, Rician, and Poisson distributions for MR, ultrasound, and CT imaging modalities respectively. In some embodiments, the added noise may be pseudo-random instead of truly random.

In some examples, the corruption includes adding spatial warping. Medical images are often distorted spatially. For example, in MR, spatial distortions may be due to off-resonance in the image, tissue specific resonance frequencies, or due to hardware (e.g., non-linear gradients). Spatial warping may be applied to the target images, then, by applying an affine transformation.

Further, in some examples, the corruption includes performing Fourier truncation to generate the corrupted images. As an illustrative and non-limiting example, FIG. 7 pictorially depicts an example method 700 for transforming a target image data set (which is presented as a clean MR-like image) into a corrupted image dataset (which is presented as a blurred MR image) by performing Fourier truncation. A Fourier transformation 707 is applied to a target image data set presented as image 705 to transform the target image data set into the k-space representation 710 of the target image 705. Then a truncation or zeroing 712 of the k-space 710 is applied to obtain truncated k-space 715. Inverse Fourier transformation is performed on the truncated k-space 715 to obtain the corrupted image data set presented as a low-resolution image 720. Mathematically, method 700 may be expressed as:

$$I_m = F^* U F I,$$

where F and F* are the forward and conjugate (inverse) Fourier operators, respectively, U is a masking (or truncating) operator, I is the input image 705, and $I_m$ is the output image 720. It should be appreciated that the image does not need to be symmetrically truncated on all four sides in k-space. For example, in some examples, one side (e.g., top or bottom, left or right) of k-space may not be acquired. Another technique for generating such low-resolution images is by convolving the high-resolution input image with a Sinc function. Mathematically, this is the same as multiplying by a rectangular function in k-space, similar to the truncated k-space 715.

Referring back to FIG. 5, method 500 continues to 515 after applying the corruption to the plurality of target image data sets to generate the plurality of corrupted image data sets. At 515, a deep neural network is trained with the plurality of pairs of target and corrupted image data sets. For example, a deep neural network, such as the deep neural network 200 described hereinabove with regard to FIG. 2, is trained to map each of the plurality of corrupted image data sets (i.e., as input of the deep neural network) to the corresponding target image data set (i.e., as output of the deep neural network), such that the deep neural network 200 learns a mapping from corrupted image data sets to target image data sets. As one illustrative and non-limiting example, method 500 may specifically utilize backpropagation to calculate and adjust weights of the deep neural network 200 to learn the mapping between the plurality of noise images and the plurality of target images. Method 500 then returns.

After training the deep neural network according to the method 500 of FIG. 5, the deep neural network may thus be used to post-process medical images acquired by a medical imaging system. As an illustrative example, FIG. 8 shows a high-level flow chart illustrating an example method 800 for post-processing an image with a trained neural network according to an embodiment. In particular, method 800 relates to post-processing a medical image with a deep neural network trained on a plurality of non-medical images as described hereinabove. Method 800 is described with regard to the systems and components of FIGS. 1-3, as well as the method of FIGS. 4 and 5, though it should be appreciated that the method 800 may be implemented with other systems, components, and methods without departing from the scope of the present disclosure. Method 800 may be implemented in non-transitory memory of a computing device, such as the data processing unit 31 of the MRI apparatus 10.

Method 800 begins at 805. At 805, method 800 acquires a medical image with a medical imaging apparatus. For example, for MRI, method 800 acquires an MR image via the MRI apparatus 10. As another example, for ultrasound imaging, method 800 acquires an ultrasound image via an ultrasound transducer probe. As yet another example, for CT imaging, method 800 acquires a CT image via a CT imaging system including at least an x-ray source and a detector. As an illustrative example, FIG. 9 shows an example raw medical image 900. In particular, the raw medical image 900 comprises a sagittal view of a head of a subject acquired using an MRI apparatus such as MRI apparatus 10.

Continuing at 810, method 800 inputs the medical image acquired at 805 into a trained deep neural network to generate a de-noised image. The trained deep neural network is trained according to the method 500 described hereinabove with regard to FIG. 5, wherein a plurality of non-medical photographs are transformed into a plurality of target images and a plurality of noise images for training the deep neural network. The target images and the noise images are generated according to a specific imaging modality, as discussed hereinabove, and so in some examples the deep neural network may be specifically trained for mapping noise images to target images according to a specific imaging modality. That is, when the medical imaging apparatus at 805 comprises an MRI apparatus such as MRI apparatus 10, for example, the deep neural network is trained on a plurality of non-medical images that are transformed into MRI-like target images as well as noise images generated from the MRI-like target images according to MRI-specific noise transformations. Similarly, when the medical imaging apparatus at 805 comprises an ultrasound transducer probe, the deep neural network is trained on a plurality of non-medical images that are transformed into ultrasound-like target images as well as noise images generated from the ultrasound-like target images according to ultrasound-specific noise transformations. When the medical imaging apparatus at 805 comprises a CT imaging system, the deep neural network is trained on a plurality of non-medical images that are transformed into CT-like target images as well as noise images generated from the CT-like target images according to CT-specific noise transformations. Further, as discussed hereinabove, in some examples the deep neural network may be trained to work with multiple modalities, including MRI, ultrasound, and CT.

The deep neural network trained as described hereinabove thus generates a de-noised image from the raw medical image input at 810. For example, if the raw medical image 900 is input to the deep neural network 200 as the input 201, the deep neural network 200 outputs a de-noised image such as the corrected image 1000 depicted in FIG. 10.

At 815, method 800 outputs the de-noised image. Method 800 may output the de-noised image, for example, to a display device such as display unit 33. An operator of the imaging system may thus view the de-noised and interpolated image 1000 instead of the low-resolution noisy image 900. Additionally or alternatively, method 800 may output the de-noised image to a storage device or a picture archiving and communication system (PACS) for subsequent retrieval and/or remote review. Method 800 then returns.

A technical effect of the disclosure includes the correction of medical images with a neural network trained on non-medical images. Another technical effect of the disclosure includes the reduction of image noise and image artifacts with a neural network trained on non-medical images. Yet another technical effect of the disclosure includes the transformation of non-medical images into medical-like images and noise images. Another technical effect of the disclosure includes the acquisition of a medical image with an imaging system, and the display of the medical image with corrections applied by a neural network trained on non-medical images.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of training a neural network, the method comprising:
   transforming each of a plurality of initial image data sets not acquired by a medical imaging modality into a target image data set, wherein each target image data set is in a format specific to the medical imaging modality;
   corrupting each target image data set to generate a corrupted image data set; and
   training the neural network to map each corrupted image data set to the corresponding target image data set.

2. The method of claim 1, wherein the medical imaging modality is magnetic resonance (MR), the initial image data sets are digital photographic data sets, and transforming each initial image data set into a target image data set comprises converting color or grayscale channels of each digital photographic data set into an MR image data set of complex values.

3. The method of claim 2, further comprising adding background phase to the MR image data set of complex values.

4. The method of claim 1, wherein the medical imaging modality is MR, the initial image data sets are digital photographic data sets, and transforming each initial image data set into a target image data set comprises converting color or grayscale channels of each digital photographic data set into an MR parametric map that models one or more of proton density, relaxation time, magnetic susceptibility, chemical shift, temperature, and diffusivity.

5. The method of claim 1, wherein the medical imaging modality is ultrasound, the initial image data sets are digital photographic data sets, and transforming each initial image data set into a target image data set comprises converting color or grayscale channels of each digital photographic data set into an ultrasound parametric map that models one or more of acoustic impedance, velocity, and density.

6. The method of claim 1, wherein the medical imaging modality is computed tomography (CT), the initial image data sets are digital photographic data sets, and transforming each initial image data set into a target image data set comprises converting color or grayscale channels of each digital photographic data set into a CT parametric map that models radiation absorption.

7. The method of claim 1, wherein the imaging modality is MR, and corrupting each target image data set to generate a corrupted image data set comprises one or more of applying Fourier truncation, applying spatial warping, adding white noise, adding blurring, and adding coil sensitivity to the target image data set.

8. The method of claim 1, wherein the imaging modality is ultrasound, and corrupting each target image data set to generate a corrupted image data set comprises one or more of applying spatial shading, adding white noise, adding speckle, adding blurring, and applying spatial warping to the target image data set.

9. The method of claim 1, wherein the imaging modality is CT, and corrupting each target image data set to generate a corrupted image data set comprises one or more of adding streak artifacts, adding white noise, adding ring artifacts, and adding blurring.

10. The method of claim 1, further comprising testing the trained neural network with image data sets acquired by the medical imaging modality.

11. A system comprising:
a memory storing a neural network; and
a processor communicably coupled to the memory and configured to:
transform each of a plurality of initial image data sets not acquired by a medical imaging modality into a target image data set, wherein each target image data set is in a format specific to the medical imaging modality;
corrupt each target image data set to generate a corrupted image data set; and
train the neural network to map each corrupted image data set to the corresponding target image data set.

12. The system of claim 11, wherein the medical imaging modality is magnetic resonance (MR), the initial image data sets are digital photographic data sets, and transforming each initial image data set into a target image data set comprises converting color or grayscale channels of each digital photographic data set into an MR image data set of complex values.

13. The system of claim 12, wherein the processor is further configured to add background phase to the MR image data set of complex values.

14. The system of claim 11, wherein the medical imaging modality is MR, the initial image data sets are digital photographic data sets, and transforming each initial image data set into a target image data set comprises converting color or grayscale channels of each digital photographic data set into an MR parametric map that models one or more of proton density, relaxation time, magnetic susceptibility, chemical shift, temperature, and diffusivity.

15. The system of claim 11, wherein the medical imaging modality is ultrasound, the initial image data sets are digital photographic data sets, and transforming each initial image data set into a target image data set comprises converting color or grayscale channels of each digital photographic data set into an ultrasound parametric map that models one or more of acoustic impedance, velocity, and density.

16. The system of claim 11, wherein the medical imaging modality is computed tomography (CT), the initial image data sets are digital photographic data sets, and transforming each initial image data set into a target image data set comprises converting color or grayscale channels of each digital photographic data set into a CT parametric map that models radiation absorption.

17. The system of claim 11, wherein the imaging modality is MR, and corrupting each target image data set to generate a corrupted image data set comprises one or more of applying Fourier truncation, applying spatial warping, adding white noise, adding blurring, and adding coil sensitivity to the target image data set.

18. The system of claim 11, wherein the imaging modality is ultrasound, and corrupting each target image data set to generate a corrupted image data set comprises one or more of applying spatial shading, adding white noise, adding speckle, adding blurring, and applying spatial warping to the target image data set.

19. The system of claim 11, wherein the imaging modality is CT, and corrupting each target image data set to generate a corrupted image data set comprises one or more of adding streak artifacts, adding white noise, adding ring artifacts, and adding blurring.

20. The system of claim 11, wherein the processor is further configured to test the trained neural network with image data sets acquired by the medical imaging modality.

* * * * *